(12) United States Patent
Hijikata et al.

(10) Patent No.: US 7,659,068 B1
(45) Date of Patent: *Feb. 9, 2010

(54) CARRIER FOR GENE DETECTION AND ITS USE FOR DETECTING VALIDITY OF INTERFERON THERAPY

(75) Inventors: Minako Hijikata, Tokyo (JP); Shunji Mishiro, Tokyo (JP); Yasuhiko Oota, Tokyo (JP); Koji Hashimoto, Sagamihara (JP)

(73) Assignee: Kabushiki Kaisha Toshiba, Kawasaki-shi (JP)

( * ) Notice: Subject to any disclaimer, the term of this patent is extended or adjusted under 35 U.S.C. 154(b) by 516 days.

This patent is subject to a terminal disclaimer.

(21) Appl. No.: 11/502,556

(22) Filed: Aug. 11, 2006

Related U.S. Application Data

(60) Continuation of application No. 10/633,659, filed on Aug. 5, 2003, now abandoned, which is a division of application No. 09/813,031, filed on Mar. 21, 2001, now Pat. No. 6,667,155.

(30) Foreign Application Priority Data

Mar. 22, 2000 (JP) ............................ 2000-080955
Mar. 6, 2001 (JP) ............................ 2001-062372

(51) Int. Cl.
*C12Q 1/68* (2006.01)
(52) U.S. Cl. .......................................... 435/6; 435/91.2
(58) Field of Classification Search ........................ None
See application file for complete search history.

(56) References Cited

U.S. PATENT DOCUMENTS

| | | | |
|---|---|---|---|
| 5,837,819 A | 11/1998 | Matsumoto et al. | |
| 5,972,692 A | 10/1999 | Hashimoto et al. | |
| 6,391,558 B1 | 5/2002 | Henkens et al. | |
| 6,667,155 B2 * | 12/2003 | Hijikata et al. | 435/6 |
| 6,783,935 B2 | 8/2004 | Hijikata et al. | |
| 6,821,724 B1 | 11/2004 | Mittman et al. | |

FOREIGN PATENT DOCUMENTS

| | | |
|---|---|---|
| JP | 4021627 | 12/2007 |
| WO | WO 90/14593 | 11/1990 |
| WO | WO 94/02606 | 2/1994 |
| WO | WO 95/28492 | 10/1995 |

OTHER PUBLICATIONS

Hijikata et al. Intervirology. 2000; 43:124-127.*
Ronni et al, Journal of Interferon and Cytokine Research, 1998, vol. 18, No. 9, pp. 773-781.
Chang et al., Arch. Virol., 1991, vol. 117, pp. 1-15.
Souteyrand et al., J. Phys. Chem. B., 1997, vol. 101, pp. 2980-2985.
Kikuchi et al, European Journal of Gastroenterology and Hepatology, 1998, vol. 10, No. 101, pp. 859-863.
Hijikata et al, Intervirology, 2000, vol. 43, pp. 124-127.
Antonelli et al, Journal of Interferon and Cytokine Research, 1999, vol. 19, pp. 243-251.
Masson et al, Clinical Pharmacokinetics, 1997, vol. 32, No. 4 pp. 324-343.
Nakade et al, FEBS Letters, 1997, vol. 418, pp. 315-318.
Callat et al, ISSCC98/ Session 17/ Sensor Technology, Paper SA 17.1, Dig. Tech. Pap. IEEE ISSCC Conf. 41, 1998, pp. 272-273.
Wang et al, Analytical Chemistry 1996, vol. 68, pp. 2629-2634.
XP-002212569, Martin et al, *Homo sapiens* (subcione H84 b_9 from P1 35 h5 c8, DNA sequence, Jun. 30, 1999 (Rel. 60, Last Updated, Version 2).
XP-002212570, Kimmerley, et al., Submitted (Sep. 4, 1998) Human Genome Center, DOE Joint Genome Institute, Accession—AC005612, Version AC005612.1 GI:3540153.
XP-002212571, Bashkirov, et al., M. musculus mRNA for 5'—3' exonuclease.
XP-002212572, Iwashita S., Rattus norvegicus gene for R-ras GTPase activating protein, promoter sequence, Jul. 4, 1999, (Rel. 60, Last updated, Version 1), Submitted (Dec. 30, 1998)to the EMBL/GenBank/DDBJ databases.

* cited by examiner

*Primary Examiner*—Juliet C Switzer
(74) *Attorney, Agent, or Firm*—Oblon, Spivak, McClelland, Maier & Neustadt, L.L.P.

(57) ABSTRACT

A carrier for gene detection as a means for prediction before treatment whether interferon therapy is valid or not for a patient, a method for detection of interferon therapy for an individual, an apparatus for gene detection, and a kit for detection of validity of interferon therapy.

13 Claims, 5 Drawing Sheets

CARRIER FOR GENE DETECTION AND ITS USE FOR DETECTING VALIDITY OF INTERFERON THERAPY

CROSS-REFERENCE TO RELATED APPLICATIONS

This application is based upon and claims the benefit of priority from the prior Japanese Patent Applications No. 2000-080955, filed Mar. 22, 2000; and No. 2001-062372, filed Mar. 6, 2001, the entire contents of both of which are incorporated herein by reference.

BACKGROUND OF THE INVENTION

The present invention relates to a carrier for gene detection, a method for detecting validity of interferon therapy on individuals, a gene detecting apparatus for detecting validity of interferon therapy on individuals, and a gene detection kit for detecting validity of interferon therapy.

In recent years, patients infected with hepatitis C viruses (to be called HCV hereafter) have rapidly increased, leading to a great social problem.

Although interferon therapy has been revealed to have a certain effect on hepatitis C as well as on other viral illnesses, interferon therapy is not effective to all the infected patients, and there are not a few patients who has no sensitivity to interferon and cannot benefit from interferon therapy. Continuation of interferon therapy to such patients who exhibit no sensitivity to interferon would not only cause side effects such as fever and anemia to the patients but also delay initiation of other expected therapies.

Therefore, there has been longed for a method of predicting whether interferon therapy is effective or not to an HCV-infected patient to be treated, but such prediction has not at all been possible.

BRIEF SUMMARY OF THE INVENTION

An object of the invention is to provide a method for predicting whether interferon therapy is effective to a patient, before the treatment is effected.

According to the first aspect of the present invention, there is provided a carrier for gene detection, which comprises:
a base body; and
a polynucleotide immobilized on the base body,
the polynucleotide comprising a polynucleotide selected from the group consisting of:
(at) the polynucleotide of Sequence ID No. 1 in the sequence listing;
(bt) a modified polynucleotide derived from the polynucleotide (at) by including one or several deletions, substitutions or additions at any positions except for 455th position;
(ct) a polynucleotide containing the sequence which spans from 441st to 455th position of Sequence ID No. 1;
(dt) a polynucleotide containing the sequence which spans from 449 th to 459th position of Sequence ID No. 1; and
(et) a complementary strand of the polynucleotide selected from the group consisting of (at), (bt), (ct) and (dt) mentioned above.

According to the second aspect of the present invention, there is provided a carrier for gene detection which comprises:
a base body; and
a polynucleotide immobilized on the base body, the polynucleotide comprising a polynucleotide selected from the group consisting of:
(ag) the polynucleotide of Sequence ID No. 2 in the sequence listing;
(bg) a modified polynucleotide derived from the polynucleotide (ag) by including one or several deletions, substitutions or additions at any positions except for 455th position;
(cg) a polynucleotide containing the sequence which spans from 441st to 455th position of Sequence ID No. 2;
(dg) a polynucleotide containing the sequence which spans from 449th to 459th position of Sequence ID No. 2; and
(eg) a complementary strand of the poly nucleotide selected from the group consisting of (ag), (bg), (cg) and (dg) mentioned above.

According to the third aspect of the present invention, there is provided a carrier for gene detection which comprises:
a base body; and
a polynucleotide immobilized on the base body,
the polynucleotide comprising a polynucleotide selected from the group consisting of:
(aa) the polynucleotide of Sequence ID No. 3 in the sequence listing;
(ba) a modified polynucleotide derived from the polynucleotide (aa) by including one or several deletions, substitutions or additions at any positions except for 455th position;
(ca) a polynucleotide containing the sequence which spans from 441st to 455th position of Sequence ID No. 3;
(da) a polynucleotide containing the sequence which spans from 449th to 459th position of Sequence ID No. 3; and
(ea) a complementary strand of the polynucleotide selected from the group consisting of (aa), (ba), (ca) and (da) mentioned above.

According to the fourth aspect of the present invention, there is provided a carrier for gene detection which comprises:
a base body; and
a polynucleotide immobilized on the base body,
the polynucleotide comprising a polynucleotide selected from the group consisting of:
(ac) the polynucleotide of Sequence ID No. 4 in the sequence listing;
(bc) a modified polynucleotide derived from the polynucleotide (ac) by including one or several deletions, substitutions or additions at any positions except for 455th position;
(cc) a polynucleotide containing the sequence which spans from 441st to 455th position of Sequence ID No. 4;
(dc) a polynucleotide containing the sequence which spans from 449th to 459th position of Sequence ID No. 4; and
(ec) a complementary strand of the polynucleotide selected from the group consisting of (ac), (bc), (cc) and (dc) mentioned above.

According to the fifth aspect of the present invention, there is provided a DNA chip, which comprises:
a base body; and
a first and a second electrodes formed on the base body,
the first electrode comprising a conductive body and at least one polynucleotide immobilized on the conductive body, the polynucleotide being selected from the group consisting of (at) to (et) shown below;
(at) the polynucleotide of Sequence ID No. 1 in the sequence listing;
(bt) a modified polynucleotide derived from the polynucleotide (at) by including one or several deletions, substitutions or additions at any positions except for 455th position;
(ct) a polynucleotide containing the sequence which spans from 441st to 455th position of Sequence ID No. 1;
(dt) a polynucleotide containing the sequence which spans from 449th to 459th position of Sequence ID No. 1; and (et) a complementary strand of the polynucleotide selected from the group consisting of (at), (bt), (ct) and (dt) mentioned above, the second electrode comprising a conductive body, and at least one polynucleotide immobilized on the conductive body, the polynucleotide being selected from the group consisting of (ag) to (eg), (aa) to (ea), and (ac) to (ec) shown below;

(ag) the polynucleotide of Sequence ID No. 2 in the sequence listing;

(bg) a modified polynucleotide derived from the polynucleotide (ag) by including one or several deletions, substitutions or additions at any positions except for 455th position;

(cg) a polynucleotide containing the sequence which spans from 441st to 455th position of Sequence ID No. 2;

(dg) a polynucleotide containing the sequence which spans from 449th to 459th position of Sequence ID No. 2;

(eg) a complementary strand of the poly nucleotide selected from the group consisting of (ag), (bg), (cg) and (dg) mentioned above;

(aa) the polynucleotide of Sequence ID No. 3 in the sequence listing;

(ba) a modified polynucleotide derived from the polynucleotide (aa) by including one or several deletions, substitutions or additions at any positions except for 455th position;

(ca) a polynucleotide containing the sequence which spans from 441st to 455th position of Sequence ID No. 3;

(da) a polynucleotide containing the sequence which spans from 449th to 459th position of Sequence ID No. 3;

(ea) a complementary strand of the polynucleotide selected from the group consisting of (aa), (ba), (ca) and (da) mentioned above;

(ac) the polynucleotide of Sequence ID No. 4 in the sequence listing;

(bc) a modified polynucleotide derived from the polynucleotide (ac) by including one or several deletions, substitutions or additions at any positions except for 455th position;

(cc) a polynucleotide containing the sequence which spans from 441st to 455th position of Sequence ID No. 4;

(dc) a polynucleotide containing the sequence which spans from 449th to 459th position of Sequence ID No. 4; and (ec) a complementary strand of the polynucleotide selected from the group consisting of (ac), (bc), (cc) and (dc) mentioned above.

According to the sixth aspect of the present invention, there is provided a method for detecting validity of interferon therapy for an individual, the method comprises:

1) contacting a polynucleotide sample taken from the individual with the carrier for gene detection according to the present invention; and 2) determining the nucleotide sequence of the polynucleotide in the sample, by detecting the hybridization reaction between the polynucleotide sample and the polynucleotide immobilized on the carrier for gene detection.

Further, according to the seventh aspect of the present invention, there is provided a method for detecting validity of interferon therapy for an individual, the method comprises:

1) contacting the probe polynucleotide to a carrier for gene detection which has a polynucleotide sample taken from the individual immobilized on a substrate; and 2) determining the nucleotide sequence of the polynucleotide sample by detecting the hybridization reaction between the polynucleotide sample immobilized on the substrate and the probe polynucleotide;

The probe polynucleotide comprises a polynucleotide selected from the group consisting of:

(at) the polynucleotide of Sequence ID No. 1 in the sequence listing;

(bt) a modified polynucleotide derived from the polynucleotide (at) by including one or several deletions, substitutions or additions at any positions except for 455th position;

(ct) a polynucleotide containing the sequence which spans from 441st to 455th position of Sequence ID No. 1;

(dt) a polynucleotide containing the sequence which spans from 449th to 459th position of Sequence ID No. 1;

(et) a complementary strand of the polynucleotide selected from the group consisting of (at), (bt), (ct) and (dt) mentioned above;

(ag) the polynucleotide of Sequence ID No. 2 in the sequence listing;

(bg) a modified polynucleotide derived from the polynucleotide (ag) by including one or several deletions, substitutions or additions at any positions except for 455th position;

(cg) a polynucleotide containing the sequence which spans from 441st to 455th position of Sequence ID No. 2;

(dg) a polynucleotide containing the sequence which spans from 449th to 459th position of Sequence ID No. 2;

(eg) a complementary strand of the poly nucleotide selected from the group consisting of (ag), (bg), (cg) and (dg) mentioned above;

(aa) the polynucleotide of Sequence ID No. 3 in the sequence listing;

(ba) a modified polynucleotide derived from the polynucleotide (aa) by including one or several deletions, substitutions or additions at any positions except for 455th position;

(ca) a polynucleotide containing the sequence which spans from 441st to 455th position of Sequence ID No. 3;

(da) a polynucleotide containing the sequence which spans from 449th to 459th position of Sequence ID No. 3;

(ea) a complementary strand of the polynucleotide selected from the group consisting of (aa), (ba), (ca) and (da) mentioned above;

(ac) the polynucleotide of Sequence ID No. 4 in the sequence listing;

(bc) a modified polynucleotide derived from the polynucleotide (ac) by including one or several deletions, substitutions or additions at any positions except for 455th position;

(cc) a polynucleotide containing the sequence which spans from 441st to 455th posit on of Sequence ID No. 4;

(dc) a polynucleotide containing the sequence which spans from 449th to 459th position of Sequence ID No. 4; and (ec) a complementary strand of the polynucleotide selected from the group consisting of (ac), (bc), (cc) and (dc) mentioned above.

According to the eighth aspect of the present invention, there is provided a gene detecting apparatus for detecting validity of interferon therapy, the apparatus comprising:

the carrier for gene detection of the present invention described above;

a reaction section for contacting a first polynucleotide immobilized on a base body of the carrier with a sample which contains a second polynucleotide labeled with a marker, and putting the first and the second polynucleotides under hybridization reaction condition; and a marker-detecting apparatus for detecting the marker attached to the second polynucleotide.

According to the ninth aspect of the present invention, there is provided a gene detection apparatus for detecting validity of interferon therapy, the apparatus comprising:

a carrier for gene detection of the present invention described above, which is used as an electrode;

a counter electrode;

a voltage application means for applying voltage between the carrier for gene detection and the counter electrode, a reaction section for contacting a first polynucleotide immobilized on a base body of the carrier with a sample which contains a second polynucleotide, and putting the first and the second polynucleotides under hybridization reaction condition; and a measurement section for measuring an electric signal generated between the carrier for gene detection and the counter electrode when voltage is applied by the voltage applying means after the hybridization reaction.

According to the tenth aspect of the present invention, there is provided a kit for determining validity of interferon therapy, which comprises the carrier for gene detection described above and a buffer solution.

According to the eleventh aspect of the present invention, there is provided a kit for detecting validity of interferon therapy for an individual, which comprises the carrier for gene detection described above, a double-strand recognizer, and a buffer solution.

DETAILED DESCRIPTION OF THE INVENTION

Figure 1:
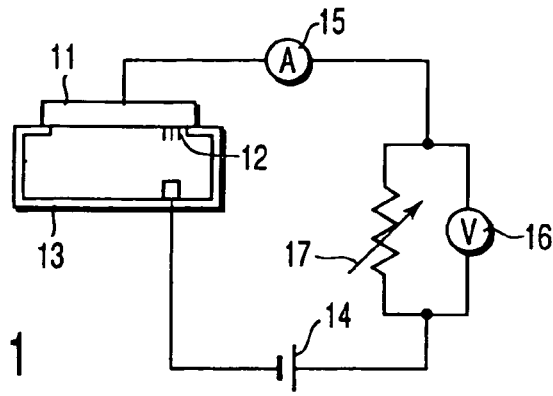
FIG. 1 shows an apparatus for gene detection according to an embodiment of the present invention.

Polynucleotides of Sequence ID Nos. 1, 2, 3 and 4 are those containing promoter regions of human MxA genes, and it was found for the first time by the present inventors that the single nucleotide polymorphism (to be called SNP hereafter) existing at 455th position of these polynucleotides contributes to responsibility to the effect of interferon therapy.

The interferon-stimulated response element (to be called ISRE hereafter) exists from 441st to 456th position of each polynucleotide.

The nucleotide sequence of ISRE from 441st to 456th position of Sequence ID No. 1 is [GGTTTCGTTTCTGCTC] (Sequence ID No. 5). The 15th position of ISRE (corresponding to 455th position of Sequence ID No. 1) is thymine. Note that according to the ordinary representation in which the transcription initiation site is referred to as +1st position, 455th position in Sequence ID No. 1 is designated as −88th position.

The nucleotide sequence of ISRE from 441st to 456th position of Sequence ID No. 2 is [GGTTTCGTTTCTGCTC] (Sequence ID No. 6). The 15th position of ISRE (corresponding to 455th position of Sequence ID No. 1) is guanine. Note that according to the ordinary representation in which the transcription initiation site is referred to as +1st position, 455th position in Sequence ID No. 1 is designated as −88th position.

The nucleotide sequence of ISRE from 441st to 456th position of Sequence ID No. 3 is [GGTTTCGTTTCTGCGC] (Sequence ID No. 7) and the 15th position of ISRE (corresponding to 455th position of Sequence ID No. 3) is adenine. Note that according to the ordinary representation in which the transcription initiation site is referred to as +1st position, 455th position in Sequence ID No. 3 is designated as −88th position.

The nucleotide sequence of ISRE from 441st to 456th position of Sequence ID No. 4 is [GGTTTCGTTTCTGCCC] (Sequence ID No. 8) and the 15th position of ISRE (corresponding to 455th position of Sequence ID No. 4) is cytosine. Note that according to the ordinary representation in which the transcription initiation site is referred to as +1st position, 455th position in Sequence ID No. 4 is designated as −88th position.

Hereinafter throughout the present specification, 455th position of Sequence ID Nos. 1, 2, 3, and 4 are called the SNP site.

The regions of these ISRE except for said SNP sites are common for each sequence. It was epidemiologically proved that while interferon therapy is effective for HCV-infected patients having ISRE (Sequence ID No. 5) in which the 15th nucleotide is thymine, interferon therapy is not effective for HCV-infected patients not having ISRE (Sequence ID No. 5) in which the 15th nucleotide is thymine.

In other words, as described in detail in examples described later, it was proved that interferon therapy is less effective for HCV-infected patients possessing homozygous promoter region comprising the polynucleotide of Sequence ID No. 2 which has guanine at 455th position (to be referred to G/G homo hereinafter), in comparison with those possessing heterozygous promoter regions comprising the polynucleotide of Sequence ID No. 1 which has thymine at the 455th position and the polynucleotide of Sequence ID No. 2 which has guanine at the 455th position (to be referred to G/T hetero hereinafter), or those having homozygous promoter region comprising the polynucleotide of Sequence ID No. 1 (to be referred to T/T homo hereinafter).

Alternatively, the interferon therapy was shown to be less effective for HCV-infected patients having homozygous promoter regions of MxA genes which has not thymine at the 455th position (to be referred to non-T/non-T homo hereinafter), in comparison with those with T/non-T hetero or T/T homo. There are G/G, G/A, G/C, A/A, A/C, and C/C as combinations of non-T/non-T homo. Combinations of T/non-T include T/G, T/A, and T/C.

Therefore, validity of interferon therapy for an HCV-infected patient can be detected prior to implementation of interferon therapy, for example by determining the nucleotide of the SNP site in ISRE of the polynucleotide which contains promoter regions of human MxA gene possessed by HCV-infected patients.

In the carrier for gene detection according to the present invention, the polynucleotide of Sequence ID No. 1 having thymine at the SNP site, a fragment or a complementary strand thereof is used as a probe for detecting sequence of nucleic acid strand of the polynucleotide extracted from a subject.

Use of the carriers for gene detection, etc. of the present invention allows examination whether said SNP site in the promoter region of human MxA gene from the subject is thymine or not, thereby enabling prediction of validity of interferon therapy for the subject.

Also, in the carriers for gene detection of the present invention, the polynucleotide of Sequence ID No. 2 having guanine at the SNP site, a fragments or a complementary strand thereor; the polynucleotide of Sequence ID No. 3 having adenine at the SNP sites, a fragments or a complementary strand thereof; and the polynucleotide of Sequence ID No. 4 having cytosine at the SNP sites, a fragment or a complementary strand thereof are used as probes for detecting the nucleic acid sequence of polynucleotides extracted from the subject.

Use of the carrier for gene detection according to an embodiment of the present invention allows identification of the nucleotide at the SNP site of the promoter regions of human MxA gene from the subject, thereby enabling prediction of validity of interferon therapy on the subject.

Besides hepatitis C, examples of diseases possibly requiring interferon therapy include glioblastoma, medulloblastoma, astrocytoma, malignant melanoma of the skin, hepatitis B, renal carcinoma, multiple myeloma, hairy cell leukemia, chronic myeloid leukemia, subacute screlosing panencephalitis, viral encephalitis, systemic herpes zoster and varicella of immunologic inhibition patients, undifferentiated epiphoryngeal carcinoma, viral internal ear infection disease accompanying hearing ability degradation, herpetic keratitis, flat condyloma, conjunctivitis due to adenovirus and herpesvirus, herpes progenitalis, herpes labialis, carcinoma uterine cervix, hepatic hydrothorax, keratoacanthoma, basal cell carcinoma, and delta chronic active hepatitis are included in diseases. Interferons used in the interferon therapy include interferon α, β, and ω, and so on.

The carrier for gene detection of the present invention can be used to detect the validity of interferon therapy prior to applying the therapy to the patients suffered from these diseases mentioned above.

Next, the aspects of the present invention are described in more detail.

First, the present invention provides a carrier for gene detection, which can be used to detect validity of interferon therapy for the patient suffered from the disease indicated for interferon therapy, prior to implementation of the therapy.

<Outline of a Carrier for Gene Detention>

The carrier for gene detection according to the embodiment of the present invention can be prepared by immobilizing the predetermined polynucleotide on a base body such as a substrate board, porous body, a microtiter plate, a particle and beads etc.

Materials, size, and shape of the base body on which the polynucleotide is immobilized are not limited, and any base body capable of being immobilized with the polynucleotide can be used.

Examples of the material for the base body include, for example, inorganic materials such as silicone, glass, crystal glass, alumina, sapphire, forsterite, silicon carbide, silicon oxide, silicon nitride, and magnetic materials, and organic materials such as polyethylene, polypropylene, polyisobutylene, polyethylene terephthalate, unsaturated polyester, fluorine-containing resins, polyvinyl chloride, polyvinylydene chloride, polyvinyl acetate, polyhvinyl alcohol, polyvinyl acetate, acrylic resin, polyacrylonitrile, polystyrene, acetal resin, polycarbonate, polyamide, phenolic resin, urea resin, epoxy resin, melamine resin, styrene-acrylonitrile copolymer, acrylonitrile-butadiene-styrene copolymer, silicone resin, polyphenylene oxide, polysulfone, nitrocellulose, nylon, polymethyl methacrylate, polyphenylenesulphone, polyethersulphone, polyether ketone, fluoroethylene copolymer, polymethylpentene. Further, composites of above mentioned inorganic and organic materials can be used.

As a method for immobilizing the polynucleotide on the base body, the method disclosed in Science 251:767773 (1991) can be used. In addition to this method, an improved method for immobilizing the polynucleotide on the base body is known, and can also be used for immobilizing the polynucleotide on the base body.

When the base body made of organic material or glass is used, stable immobilization of the polynucleotides can be attained by coating the surface of the base body with polylysine or aminosilane.

In the present specification, "polynucleotide" means chemical substances formed by coupling two or more nucleosides through phosphate bonds. "Nucleosides" include, but not limited to, deoxyribonucleoside and ribonucleosides.

Furthermore, examples of the polynucleotide to be immobilized on the base body of the present invention include RNA, DNA, PNA, methyl phosphonate nucleic acids, oligonucleotide such as S-oligo, and polynucleotides such as cDNA, and cRNA.

In the present specification, "promoter region" indicates not only the region directly involved in transcription initiation reaction such as TATA box, but also sequences including control sequences that exist in close proximity of or distant from said region to influence the efficiency of the transcription initiation reaction. Therefore, it should be noted that the term "promoter region" includes a sequence involved in transcription initiation reaction alone, a control sequence alone, and a conjugated sequence between the both sequences.

Incidentally, "ISRE" means a nucleotide sequence consisting of about 12 to 15 nucleotides which exist in the transcription control region of the gene induced by the stimulus of interferon α, β, γ, or ω).

Examples of the polynucleotide, which can be immobilized on the base body according to the present invention, include the polynucleotide selected from the group consisting of the following (a) to (e).

(a) Polynucleotide indicated by any one of Sequence ID Nos. 1, 2, 3, or 4.

(b) A modified polynucleotide derived from the polynucleotide listed in (a) by including one or several deletions, substitutions or additions at any positions except for 455th position.

Examples of the deletion, substitution and addition include deletion at 128th, 133rd, 152nd, 508th, and 543rd position, substitution at 330th position (G→T), and addition at 501st position.

Furthermore, it is possible to use a combined polynucleotide in which the polynucleotide of the Sequence ID Nos. 1, 2, 3, or 4 or fragments thereof is conjugated with at least one functional polynucleotide selected from the group consisting of promoters, enhancers, upstream activation sequence, silencers, upstream suppression sequence, attenuators, poly A tail, nucleus transition signals, Kozak sequence, ISRE, drug resistance factors, genes of signal peptide, genes of transmembrane domains, luciferin-gene, green fluorescent protein gene, phycocianin gene, genes of marker protein containing horseradish peroxidase, genes of interferon-responding protein, and genes of interferon-non-responding protein.

Further, in the nucleotide sequences of said polynucleotides of Sequence ID Nos. 1, 2, 3, and 4, only one nucleotide at the SNP site (located at 455th position) is involved in the validity of interferon therapy. Therefore, the polynucleotide to be immobilized on the base body can be a fragment of said polynucleotide containing the SNP site at the 455th position.

When said fragment is used as the polynucleotide to be immobilized on the base body, it is preferably of length not shorter than 11 nucleotides and no longer than 30 nucleotides. More preferably, it is of length not shorter than 15 nucleotides. When the polynucleotide to be immobilized on the base body is too long, it is difficult to identify difference of one nucleotide. On the other hand, when the polynucleotide to be immobilized on the base body is too short, it is difficult to hybridize with and determine the nucleotide sequence of the polynucleotide included in the sample.

Particularly preferable polynucleotides to be immobilized on the base body are:

(c) A fragment of polynucleotide of Sequence ID Nos. 1, 2, 3, or 4 including the SNP site at the 455th position, a fragment containing the polynucleotide of Sequence ID Nos. 5, 6, 7, or 8 (namely said ISRE) corresponding to the sequence from 441st to 456th position of Sequence ID Nos. 1, 2, 3, or 4.

(d) A fragment of polynucleotides of Sequence ID Nos. 1, 2, 3, or 4 including said 455th SNP site, a fragment containing the polynucleotide of Sequence ID Nos. 9, 10, 11, or 12 corresponding to the sequence from 449th to 459th position of Sequence ID Nos. 1, 2, 3, or 4. Particularly, since the fragment (d) has said SNP site roughly at the center thereof and contains nucleotide sequences of equal length on both sides, high-precision determination of nucleotide sequence can be achieved. In order to carry out detection of still higher precision, a fragment including the polynucleotide corresponding to the sequence from 447th to 461st position of Sequence ID Nos. 1 to 4 are preferable.

Furthermore, a polynucleotide to be immobilized on the base body can be:

(e) A complementary strands of polynucleotide selected from the group consisting of (a), (b), (c) and (d) described above.

Note that complementary strands of the polynucleotides indicated by Sequence ID Nos. 5, 6, 7, and 8 (i.e., the ISRE) are the polynucleotide strands of Sequence ID Nos. 13, 14, 15, and 16, respectively.

Note that complementary strands of the polynucleotide indicated by Sequence ID Nos. 9, 10, 11, and 12 are the polynucleotide strands of Sequence ID Nos. 17, 18, 19, and 20, respectively.

The carriers for gene detection according to the embodiment of the present invention are used in order to detect hybridization reaction of the polynucleotide extracted from the subject with a probe using the predetermined polynucleotide immobilized on the base body as the probe, to determine the polynucleotide sequence containing promoter region of human MxA gene of the subject, and to examine what type of nucleotide is exist at the SNP site.

<Method for Using Carriers for Gene Detection>

The method for determining sequences of polynucleotides extracted from a subject by using said carrier for gene detection is particularly explained.

In order to perform sequencing of polynucleotides extracted from a subject by using said carrier for gene detection, there can be two kinds of methods: (1) the method using a marker substance and (2) the electrochemical method.

First, (1) the method using a marker substance is specifically explained.

Samples containing polynucleotides (body fluid such as blood, blood cells, biopsy tissue, or cultured cells) are taken from a subject of an individual, which is a mammal including humans, for example. They can be arbitrary samples taken from an individual since polynucleotides are widely distributed in the body. A preferable sample is blood.

Then, if necessary, extraction and separation processes such as phenol extraction and ethanol precipitation is performed. Subsequently, amplifying processes such as PCR are carried out, and then, the sample polynucleotides contained in said sample are extracted. For extracting the sample polynucleotides, optional extraction methods can be used other than phenol extraction and ethanol precipitation, for example. When m RNA is extracted, oligo dT column can be used. When the amount of sample polynucleotide is small, optional amplification of the sample polynucleotides may be carried out, if necessary.

Then, labeling procedure is carried out to provide the sample polynucleotide labeled with the marker. Alternatively, secondary probe containing polynucleotides labeled with the marker substances can be mixed instead of labeling the sample polynucleotide.

As detectable markers, use can be made of, but not limited to, light emitting substances such as fluorescent substances, hapten, enzymes, radio isotopes, and electrode active substances. Labeling of sample polynucleotides is preferably performed for labeling the promoter region. Various known methods can be used to label the promoter region. In particular, PCR reaction using labeled primers may be useful since amplification and labeling can be carried out simultaneously.

Then, the sample polynucleotides are subjected to the hybridization reaction with the polynucleotide-immobilized base body of the gene detection carrier. In other words, after said labeled sample polynucleotide is first added to the reaction solution for hybridization, said reaction solution is contacted with the gene detection carrier. When the sample contains a certain polynucleotide complementary to the polynucleotide strand immobilized on the base body, the sample polynucleotide is hybridized with the polynucleotide on the base body and immobilized thereon.

Regarding the condition of the hybridization reaction, reaction temperature may range from 10 to 90° C. and reaction time may range from 1 minute or longer to overnight. During the reaction, the reaction rate can be accelerated by operations such as agitation and shaking. The reaction solution for the hybridization can be buffer solutions with ionic intensity in the range of 0.01-5, and pH in the range of 5-10. Hybridization promoters such as dextran sulfate, salmon sperm DNA, bovine pectus DNA, EDTA, and surfactants can be added to the reaction solution.

Afterwards appropriate washing is carried out.

Then, in order to determine what type of nucleotide the subject possesses at said SNP site, detection is made for finding if the hybridization reaction between the sample polynucleotide and the polynucleotide on the base body has took place or not.

If the sample polynucleotide is detected to have been hybridized to a polynucleotide which has thymine at the SNP site or its complementary strand among the polynucleotides (a) to (e) immobilized on the base body, the SNP site of the polynucleotide which contains the promoter region of the subject's human MxA gene is thymine. On the other hand, if the sample polynucleotide is detected to have been hybridized to a polynucleotide which has guanine at the SNP site or its complementary strand, the SNP site of the polynucleotide which contains the promoter region of the subject's human MxA gene is guanine. The same is held true for the cases of adenine and cytosine.

This detection is carried out by detecting the marker in the labeled polynucleotide or the labeled secondary probe in the sample, using an appropriate detection apparatus depending on the kind of labeling markers. For example, when the marker is a fluorescent substance, the marker can be detected using a fluorescence detector. The carrier for gene detection may comprise any polynucleotide selected from the group consisting of the polynucleotide (a) to (e) described above immobilized on the base body. Specifically, the polynucleotide can be at least one polynucleotide selected from the group consisting of the polynucleotide having thymine at the SNP site or its complementary strand, the polynucleotide having guanine at the SNP site or its complementary strand, the nucleotide having adenine at the SNP site or its complementary strand, and the polynucleotide having cytosine at the SNP site or its complementary strand. In this case, however, it is required that the SNP type of the polynucleotide immobilized on the base body, as well as at least one of the address of each polynucleotide on the base body surface and type of marker should be determined in advance. At least one of the address and the type of the detectable marker enables to determine which polynucleotide on the base body has hybridized with the polynucleotide of the sample.

In the method (1) using the marker substance, the sequence of the sample polynucleotide can be determined even when the sample polynucleotide taken from the subject is immobilized on the base body of the carrier for gene detection. Namely, the sample polynucleotide immobilized on the base body are contacted with solutions of polynucleotides selected from (a) to (e) described above which has known sequences and labeled in advance with different markers based on the difference of said SNPs, in order to put the both polynucleotides under the hybridization reaction condition. If a polynucleotide strand complementary to the sample polynucleotide immobilized on the base body is contained in the solution, the complementary polynucleotide strand is hybridized with the sample polynucleotide on the base body and is immobilized on the base body. Thereafter, by detecting the type of marker substance immobilized on the base body, it is possible to detect which polynucleotide has been hybridized with the sample polynucleotide, and further, to know the sequence of the sample polynucleotide based on the known sequence of the labeled polynucleotide.

In the method mentioned above, when the sample polynucleotide hybridized with the labeled polynucleotide having thymine at SNP site or its complementary strand, the subject has thymine at said SNP site, and therefore, it can be predicted that the interferon therapy is valid in the subject. On the other hand, when the sample polynucleotide hybridized with the labeled polynucleotide having thymine at SNP site or its complementary strand, and did not hybridize with the labeled nucleotide having thymine at SNP site, the subject does not have thymine at said SNP site, and therefore, interferon therapy can be predicted to be invalid.

Next, the electrochemical method (2) is particularly explained.

In contrast to the method (1) in which hybridization reaction between the sample polynucleotide and the probe polynucleotide is determined by detection of marker substances as described above, the electrochemical method (2) electrochemically detects the hybridization reaction.

In the electrochemical method, a polunucleotide-immobilized electrode is used as the carrier for gene detection. The polynucleotide-immobilized electrode (to be referred as the electrode of the present invention hereafter) comprises a base body made of conductive material, and at least any one of the polynucleotides (a) to (e) described above immobilized on the base body.

Although preferable conductive material for the base body is gold, other materials can be used. For example, gold alloy, elemental metals and their alloys such as silver, platinum, palladium, silicon, germanium, gallium, tungsten, and carbons such as graphite and glassy carbon, as well as their oxides and compounds can be used. These conductive materials can be formed on a separate substrates as a film by plating, printing, sputtering and vapor deposition.

The method of immobilizing polynucleotide on the base body made of conductive material is not especially limited. For example, the immobilization can be easily carried out by utilizing the affinity bond between thiol groups introduced in the polynucleotides and gold surface of the base body. In addition, the immobilization may be possible by physical adsorption, chemical adsorption, hydrophobic bonding, embedding, and covalent bonding. Further, biotin-avidin bonding and use of condensation agents such as carbodiimides can be employed. In these cases, the immobilization can be facilitated when the conductive surface of the base body is modified with molecules having functional groups. Further, in order to suppress non-specific adsorption of polynucleotides on the surface of the base body, the surface is desirably coated with mercaptans such as mercaptoethenol or lipids such as stearylamine.

As an example, a method for immobilizing polynucleotide on a gold base body is described below. First the gold base body is subjected to activation treatment after it was rinsed with deionized water. A sulfuric acid solution of 0.1 to 10 mmol/L is used for the activation. In this solution, voltage is scanned in the ranges of −0.5 to 2 V (vs Ag/AgCl) and 1 v/s to 100000 v/s. This treatment activates the surface of the gold substrate to the condition under which polynucleotides can be immobilized thereon.

On the other hand, thiol groups are introduced at the 5' and the 3' ends of the probe polynucleotides to be immobilized. The thiolated polynucleotides are kept dissolved in a solution of a reducing agent such as DTT, and the DTT is removed just before use by gel filtration or ethyl acetate extraction. For immobilization, a probe is dissolved in the range of 1 ng/mL to 1 mg/mL in a buffer solution of ionic intensity of 0.011 to 5 and pH of 5 to 10, and the substrate just after activation is immersed in the solution. The immobilization reaction is carried out at 4 to 100% for 10 minutes to overnight. The base body after polynucleotide immobilization is desirably kept under the condition that nucleic acid decomposing enzymes (nuclease) are absent, and possibly in the dark.

When immobilizing polynucleotides on a base body, immobilizing apparatuses such as the DNA spotter and the DNA arrayer can be used to immobilize polynucleotides relatively easily. A spotter of ink-jet type or static electricity type is desirably used to avoid damaging the surface of the substrate. Further, it is possible to synthesize the polynucleotides directly on the substrate.

It is desirable that the electrode of the present invention is constructed as so called DNA chip in which the conductor and the electrode electrically connected, and are arranged on a same base body. The DNA chip is manufactured by arranging the conductors such as metal wirings appropriately coated with insulating materials on the base body (desirably an insulating base body), followed by electrically connecting the electrode (on which the predetermined polynucleotides are previously immobilized) to the conductors.

Polynucleotides of different sequences need to be immobilized on plurality of different electrodes that are insulated with each other. In arranging plurality of electrodes on a base body, the number of electrodes to be arranged on a substrate can practically be $10^1$ to $10^5$.

When plurality of electrodes of the present invention are arranged on a same base body, scanning lines can be further arranged to locate switching elements on each crossings of said conductors and the scanning lines. This enables quick determination of whether hybridization reaction occurred or not for each electrode, by applying voltage on one electrode after another. In detection of occurrence of hybridization reaction using the electrode, at least a counter electrode, and a reference electrode, if necessary, is provided in the same manner as in other ordinary electrochemical detection methods. When the reference electrode is employed, ordinary reference electrode such as silver/silver chloride-electrode, and mercury/mercury chloride electrode can be used. These electrodes are desirably arranged on the same base body as the electrode of embodiment of the present invention is arranged.

In order to determine the sequence of the polynucleotides sampled from subjects using the electrode of the present invention, following operations are carried out.

First, a sample polynucleotide is taken from a subject such a mammal including humans, for example, to which above mentioned extraction, amplification and labeling with a marker are optionally carried out. These procedures are same as in the method (1). However, labeling is not necessarily required.

Next, the solution containing said sample is put in contact with the electrode to place the sample polynucleotide and the polynucleotide immobilized on the base body under the condition of hybridization reaction. In case that the complementary strand of the polynucleotide on the base body is contained in the sample polynucleotide, the complementary sample polynucleotide is hybridized with the polynucleotide immobilized on the base. The procedure and the condition are same as the method (1). Then the electrode is rinsed.

Subsequently, a solution of electro-active double strand recognizer is added in the hybridization reaction system, thereby intercalating the double strand recognizer into the double strand polynucleotide formed by hybridization of the polynucleotide immobilized on the electrode and the sample polynucleotide. Occurrence of hybridization between the sample polynucleotide and the polynucleotide immobilized on the base body can be detected by applying voltage to the electrode and the counter electrode. When the voltage is applied, the electric signal is generated from the double strand recognizer intercalated to the double strand polynucleotide which has been formed by the hybridization. Therefore, the electric signal indicate the occurrence of the hybridization.

The electro-active double strand recognizer used here is not especially limited, and for example, Hoechst 33258, acridine orange, quinacrine, daunomycin, metallo-intercalator, bisintercalators such as bisacridine, trisintercalator, poly-intercalator, and so on can be used. Complexes of metals such as ruthenium, cobalt and iron called metallo-intercalators, as well as organic compounds such as ethylene dibromide can be used. Further, groove binders such as Hoechst 33258 and cyanine dyes, and high molecular bio-substances such as antibodies and enzymes can also be used.

The concentration of the double strand recognizer varies depending upon the types, but generally used in the range of 1 ng/mL to 1 mg/mL. Here, a buffer solution having ionic intensity in the range of 0.001 to 5 and pH in the range of 5 to 10 is used.

After the electrode is reacted with the double strand recognizer, the electrode is optionally rinsed further. Subsequently, the electrode of the present invention is used as a working electrode, and voltage is applied between the working electrode and a separately provided counter electrode to detect the electrochemical signal by determining the electric current between the two electrodes. While an electrochemical signal can be detected with such two electrodes (working and counter electrodes), the detection can also be carried out using three electrodes, i.e., working, counter and reference electrodes. In detecting the electrochemical signal, the voltage can be scanned at constant speed, or applied by pulses, or constant voltage can be applied. For measurement, electric current and voltage are controlled using such apparatuses as potentiostats, digital multimeters, and function generators. The concentration of target genes may calculated from calibration curve based upon the current values obtained.

Among the polynucleotides (a) to (e) described above, the polynucleotide having thymine at the SNP site and its complementary strand, the polynucleotide having guanine at the SNP site and its complementary strand, the polynucleotide having adenine at the SNP site and its complementary strand, and the polynucleotide having cytosine at the SNP site and its complementary strand are desirably immobilized on separate electrodes which are insulated from each other and provided on the same substrate to form a DNA chip in order to carry out high-precision determination. In this case, electrochemical signal corresponding to each polynucleotide is detected from each electrode.

The sequence of the sample polynucleotide can also be determined by the electrochemical method (2) using an electrode on which the sample polynucleotide taken from a subject is immobilized. Thus, the polynucleotide in the solution and the sample polynucleotide on the electrode are put under hybridization reaction condition by contacting a solution of any one of the polynucleotides (a) to (e) in which the sequences thereof are previously known. If the complementary strand of the sample polynucleotide is contained in the solution, the complementary polynucleotide is immobilized on the base body through hybridization with the sample polynucleotide previously immobilized on the base body. The sequence of the sample polynucleotide can be known by detecting the hybridization reaction.

When the hybridization reaction of the sample polynucleotide with the polynucleotide having thymine at SNP site or its complementary strand is detected by the above mentioned method, the subject possesses thymine at SNP site, and therefore, interferon therapy can be predicted to be valid. On the other hand, when the hybridization reaction of the polynucleotide of the sample with the polynucleotide having other bases than thymine at SNP site or its complementary strand is detected, and the hybridization reaction with the polynucleotide having thymine at said SNP site or its complementary strand is not detected, the subject does not have thymine at said SNP site, and therefore, interferon therapy is detected to be invalid.

<Electric Detection Apparatus>

The followings are descriptions of an example of the gene detection apparatuses for determining the sequence of polynucleotide which is extracted from a subject using the electrode of embodiment of the present invention. Namely this is a gene detection apparatus comprising an electrode of the embodiment of the present invention, a reaction section for carrying out the hybridization reaction with the polynucleotide immobilized on the electrode, a means for applying voltage on the polynucleotide immobilized on the electrode, a means for measuring the signal generated through the action the applied voltage.

<Basic Construction of the Electric Detection Apparatus>

FIG. 1 illustrates the embodiment of such an apparatus for gene detection. In FIG. 1, 11 denotes the electrode having polynucleotide 12 immobilized-thereon. 13 denotes a reaction vessel. A power source 14 is connected so as to form a circuit through an electrode 11 and the reaction vessel 13. An ammeter 15, a voltmeter 16, and a variable resistor 17 are arranged in the circuit for enabling application of voltage and measurement of the current in the circuit after the hybridization reaction is accomplished in the reaction vessel 13.

In order to carry out detection using the apparatus for gene detection of FIG. 1, the buffer solution and the sample containing polynucleotide taken from a subject are held in the reaction vessel 13, and hybridization reaction between the sample polynucleotide and the polynucleotide 12 immobilized on the electrode 11 is carried out. The conditions of temperature and time of hybridization are as described previously. Then, after the reaction vessel 13 and the electrode 11 are preferably rinsed, the reaction vessel 13 is filled with the hybridization solution containing an intercalator. Subsequently, the power source 14 is turned on and the current or the voltage are measured using the ammeter 15 and the volt meter 16.

Figure 2:
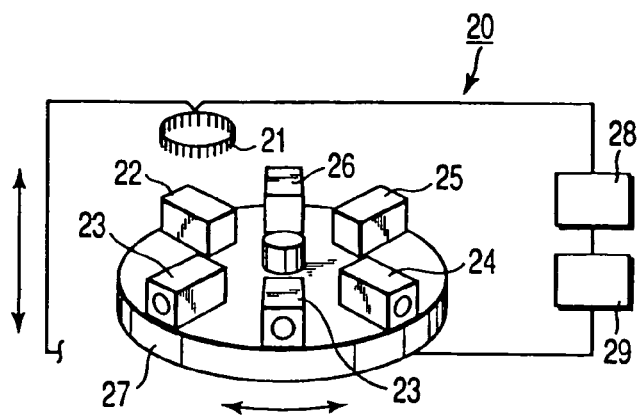
FIG. 2 shows an example of an automated electric detection apparatus according to an embodiment of the present invention.

While FIG. 1 shows the embodiment of the apparatus for gene detection of the present invention, the apparatus for gene detection of the present invention can have a more sophisticated construction as shown in FIG. 2, in order to fully automate the detection.

<Construction of Automated Electric Detection Apparatus>

The detection apparatus 20 illustrated in FIG. 2 comprises an electrode holder 21 for holding the polynucleotide-immobilized electrode, a reaction vessel 22, the first washing vessel 23, an intercalation reaction vessel 24, the second washing vessel 25, a transfer apparatus 27 carrying the electrochemical measurement vessel 26, an analysis unit 28, and an operation unit 29. Transfer of electrodes among these vessels is attained by moving the electrode using the transfer apparatus 27.

<Method for Using the Electric Detection Apparatus>

The method fox using the detection apparatus 20 is as follows.

First, the solution containing the sample or polynucleotide previously extracted from the sample is received in the reaction vessel 22, and the electrode fixed on the electrode holder 21 is immersed in the reaction vessel 22. Then, after hybridization reaction is carried out in the reaction vessel 22, the electrode holder 21 is transferred to the first washing vessel 23. Washing is carried out in the first washing vessel 23 to remove nucleic acids and proteins non-specifically bound to the electrode. After washing, the electrode holder 21 is transferred to the intercalation reaction vessel 24, for inserting the intercalator into the double strand polynucleotide formed by hybridization reaction. Then, the electrode holder 21 is transferred to the second washing vessel 25. After washing, the electrode holder 21 is further transferred to the electrochemical measurement vessel 26 to carry out electrochemical measurements. After completion of the measurements, the concentration of the polynucleotide in the sample is output in reference with the calibration line previously recorded in the analysis unit 28. The operation described above is carried out through the operation unit 29 electrically connected with each vessel and unit.

The present invention provides a kit comprising the carrier for gene detection of the present invention and a buffer solution.

It is convenient to provide the carrier for gene detection and the buffer solution in a kit since detection can be carried out right away.

The buffer solution to be used in the kit of the present invention can be an arbitrary buffer solution used in hybridization reactions. For example, use can be made of, but not limited to, phosphate buffer solution, carbonate buffer solution, and tris buffer.

Note that primers for amplification of genes, fluorescent-dye-labeled nucleotides, enzymes, columns for purification, and so on can be included to the kit together with, or in place of the buffer solutions.

The present invention provides a kit comprising the electrode of the present invention and the double strand recognizer.

The double strand recognizers to be used for the kit of the present invention can be, for example, the double strand recognizer described above with the electrode of the present invention.

Primers for amplification of genes, enzymes, buffer solutions, nucleotides, and so on can be included in the kit together with, or in place of the double strand recognizer.

The present invention will be explained below in more detail by way of examples.

EXAMPLE 1

In this example, it has been proved that HCV patients having a homozygous or heterozygous MxA gene which has thymine at 88th position (corresponding to 455th position in the nucleotide sequence of Sequence ID No. 1) in the promoter region (to be described MxA(T) hereafter) exhibit better response to interferon therapy than HCV patients having homozygous MxA gene which has guanine at that position (to be described as MxA(G) hereafter).

<Subject>

115 patients histologically proved to be suffered from chronic hepatitis C and receiving interferon therapy and 42 healthy persons with anti-HCV antibody negative took part in this study. All of them are Japanese and do not have blood relationship with each other.

Among the 115 patients, 52 were in the normal level of serum alanine aminotransferase during follow-up term of at least 6 months after completion of interferon therapy, and were sustained responders (to be described as NR hereafter) with HCV RNA always negative, and 63 patients were remained HCV RNA positive during the follow-up term independent on the ALT level, or non-responders with relapsed hepatitis C (to be called NR hereafter). Total dose of over 300 million units of interferon α and/or β were administered to all the patients.

<MxA Gene Analysis>

Nucleic acids were extracted from the BPMC sampled from the patients and the healthy controls. Said nucleic acids were subjected to PCR to amplify DNA having 599 nucleotides which contains the promoter region of MxA genes.

The outline of PCR was as follows.

After mixing 0.05 μg of nucleic acid with Taq-Gold (Perkin-Elmer), oligonucleotide primer #MXAF01 of Sequence ID No. 12 (forward primer, 569th to 540th position), and oligonucleotide primer #MXAF02 of Sequence ID No. 6 (reverse primer, 30th to 1st position), reaction was carried out under the cycle condition of [95° C./10 minutes], [95° C./10 seconds, 68° C./60 seconds]×55, [72° C./7 minutes]. By the direct sequencing of the PCR products, sequences of 12 samples out of 157 were determined.

After identification of the SNP sites in the amplified regions by sequencing, RFLP systems for the detection of nucleotides of alleles in a distinguishable manner was established. PCR products of the 599th nucleotides from all the patients were digested with HhaI(GCG↓C), and if either one or both of a 482 nucleotides-band and a 533-nucleotides band are formed or not was examined by electrophoresis in an agarose gel.

<Statistical Analysis>

Group data were compared by Fischer's precise probability test with or without Yate's correction. p<0.05 was regarded as statistically significant.

<Result>

Figure 3:
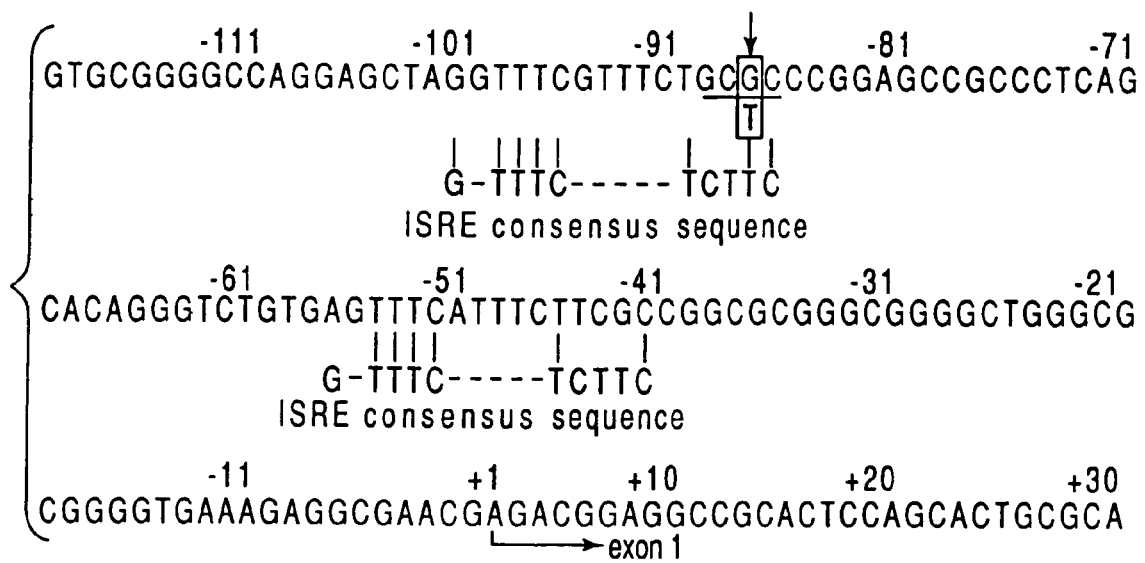
FIG. 3 shows the nucleotide sequence of the promoter region of MxA gene.

From sequencing of 12 samples, SNP sites in the promoter region of MxA genes are identified. SNP (G and T) existed at the 88th position of said promotor region, said SNP being contained in the regions similar to ISRE shown in FIG. 3.

Figure 4:
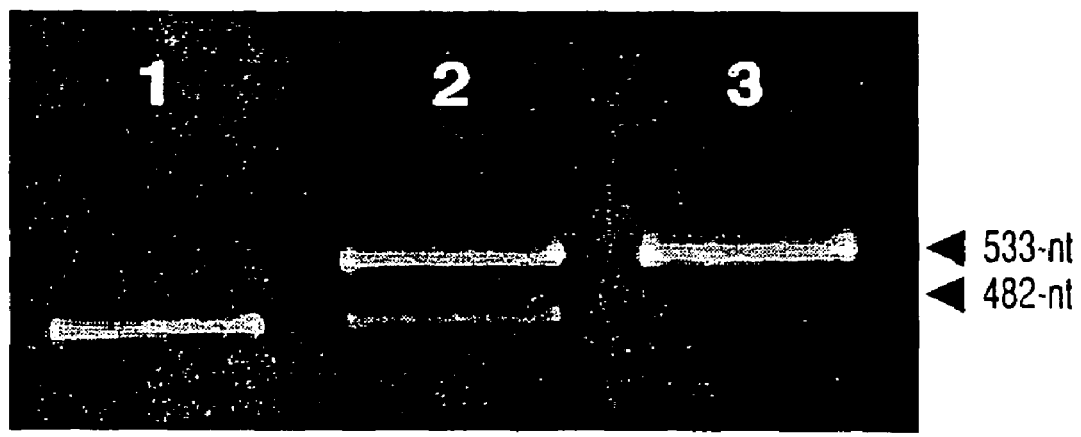
FIG. 4 shows the result of RFLP electrophoresis using HhaI according to an embodiment of the present invention.

In the RFLP by HhaI that followed, gene types of MxA genes from all the 157 samples are determined. In this assay, samples having guanine at the SNP sites showed a band of 482 base pairs in the electrophoresis gel. On the other hand, when guanine is replaced by thymine, a band of 533 base pairs appeared because the restriction site recognized by HhaI disappeared. In case of heterozygote in which the promoter region having guanine at the SNP site and the promoter region having thymine at the SNP site, both the bands of 482 and 533 base pairs are detected (see FIG. 4).

As shown in Table 1, 62% of the patients in the NR group owned the homozygous promoter region having guanine at the SNP site (G•G Homo), while 33% of the patients in the SR group were G•G Homo (p=0.0009; SR vs.NR). On the contrary, 35% of the patients in the NR group were heterozygous who posses, promoter region having guanine at the SNP site and the promoter region having thymine at the SNP site (G•T Hetero), while 60% of the patients in the SR group were G•T Hetero (p=0.0082; SR vs.NR). Patients of T•T Homo were 3.2% in the NR group and 10% in the SR group respectively (p=0.0018; SR; vs.NR).

While the frequency of alleles having promoter regions in which the SNP site is guanine was 0.606 in the SR group, it was 0.794 in the NR group (p=0.0018; SR vs.NR).

TABLE 1

| Polymorphism at −88th Position if MxA promoter | SR patient (n = 52) | NR (n = 63) | Healthy Control (n = 42) | P: SR vs NR |
|---|---|---|---|---|
| Allelic frequency | | | | |
| G | 0.606 | 0.794 | 0.714 | 0.0018 |
| T | 0.394 | 0.296 | 0.286 | 0.0018 |

TABLE 1-continued

| Polymorphism at −88th Position if MxA promoter | SR patient (n = 52) | NR (n = 63) | Healthy Control (n = 42) | P: SR vs NR |
|---|---|---|---|---|
| Zygote type | | | | |
| G · G Homo | 16(31%) | 39(62%) | 20(48%) | 0.0009 |
| G · T Hetero | 31(60%) | 22(35%) | 20(48%) | 0.0082 |
| T · T Homo | 5(10%) | 2(3.2%) | 2(4.8%) | 0.2956* |

*Yate's revision was implemented

Further the above result that individuals with G-G Homo are significantly fewer in the SR group than in the NR group was made clear to be independent of the gene types of HCV the patients were infected.

TABLE 2

| Zygote type of SNP Located at −88th position of MxA promoter | SR patient | NR patient | p: SR vs NR |
|---|---|---|---|
| Patient infected by HCV of Gene of 1b type | n = 18 | n = 42 | |
| G · G Homo | 5(28%) | 26(62%) | 0.0321* |
| G · T Hetero | 12(67%) | 14(33%) | 0.0170 |
| T · T Homo | 1(5.6%) | 2(4.8%) | 0.6051* |
| Patient infected by HCV of Gene of 2a or 2b type | n = 34 | n = 21 | |
| G · G Homo | 11(32%) | 13(62%) | 0.0318 |
| G · T Hetero | 19(56%) | 8(38%) | 0.1999 |
| T · T Homo | 4(12%) | 0 | 0.2722* |

*Yate's revision was implemented

It is apparent from Table 2 that in both of the patient group infected with HCV (HCV 1b group) of 1b gene type and the patient group infected with HCV (HCV 2a/2b group) of 2a or 2b gene type, 62% were G-G Homo individuals in the NR group, while 28% and 32% were G-G Homo individuals in the SR group. The result shown in Table 2 revealed that G•G Homo individuals are significantly fewer in the SR group independent of the gene type of HCV the patients were infected (HCV 1b group; p=0.0321, HCV 2a/2b group; p=0.0318).

In summary, the present example proved that HCV-infected patients possessing homozygous or heterozygous MxA promoter region which has thymine at the SNP site are more highly responsible to interferon therapy independent on the gene type of the infected HCV.

Further, the present example also suggests that HCV-infected patients having homozygous or heterozygous MxA promoter regions which has not guanine at the SNP site is highly responsible to interferon therapy.

Further, these finding may be applicable to diseases other than hepatitis C, since said SNP site exists in ISRE.

EXAMPLE 2

As made clear in Example 1, treatment of hepatitis by interferon administration is highly effective with HCV-infected patients whose SNP of the MxA promoter is T type. On the other hand, in case the SNP is G type, the treatment is less effective. These facts are construed as follow: while the T type of nucleotide sequence of ISRE correctly responds to the stimulus of interferon to achieve sufficient production of MxA proteins, the G type with one base different from the sequence does not respond to the stimulus of interferon resulting in less production of MxA proteins.

From this point of view of the situation, interferon therapy is also assumed to be less effective in HCV hepatitis patients having C and A types of SNP of MxA promoter, since the MxA promoters do not respond to interferon as in the case of G type.

In order to prove them, a plasmid having luciferase gene downstream of the MxA promoter was constructed and was transfected into human cells (HeLa cells and ovary cancer cells). Then, the activities of luciferase produced as the result of the response of the MxA promoter to interferon were examined in each case of MxA promoters having any one of 4 kinds of SNPs (T, G, A, and C types).

Figure 5:
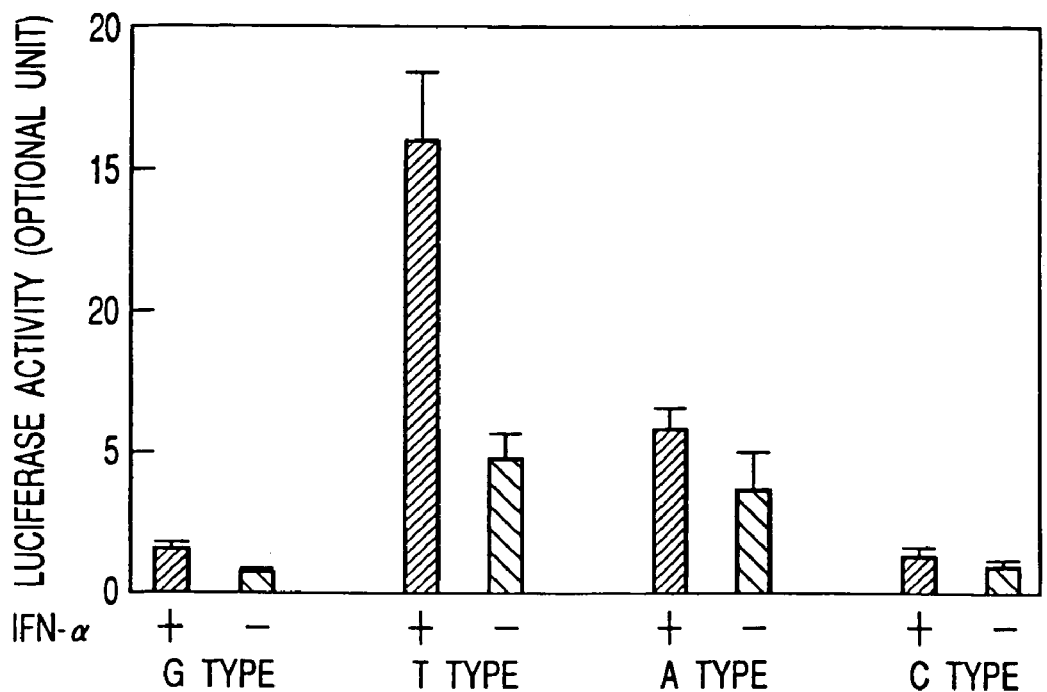
FIG. 5 is a graph showing comparison of responsibility to interferon α, among MxA promoters having four kinds of SNP (T type, G type, A type and C type). The results were obtained in Hela cells using luciferase activity under the control of said promoters.
Figure 6:
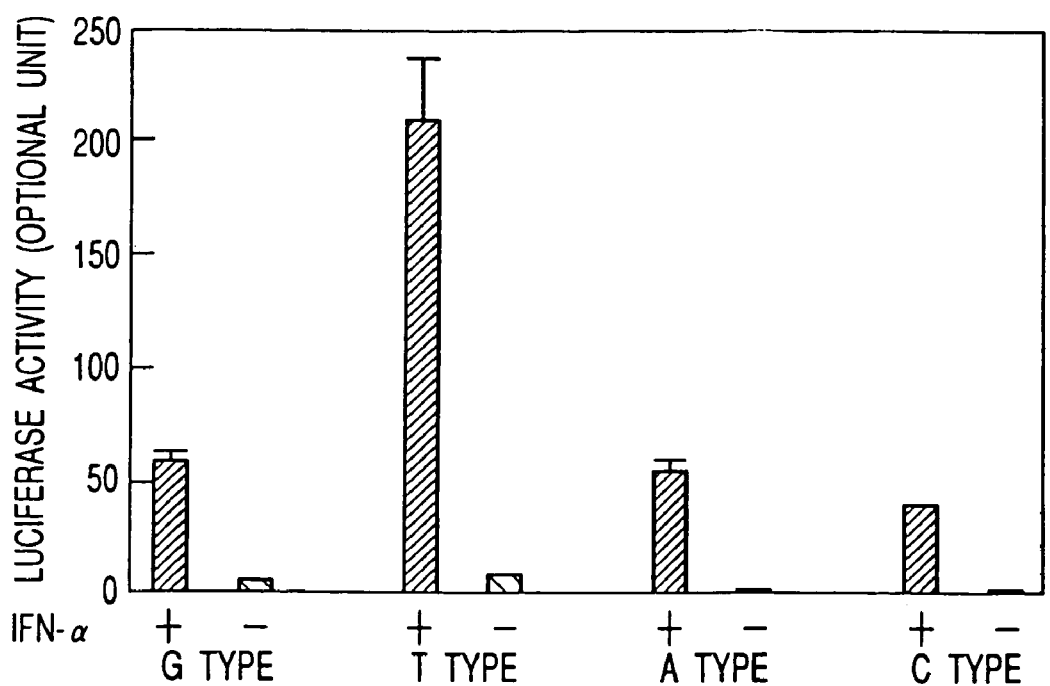
FIG. 6 is a graph showing comparison of responsibility to interferon a among MxA promoters having four kinds of SNP (T type, G type, A type and C type). The results were obtained in ovarian cancer cells using luciferase activity under the control of said promoters.
Figure 7:
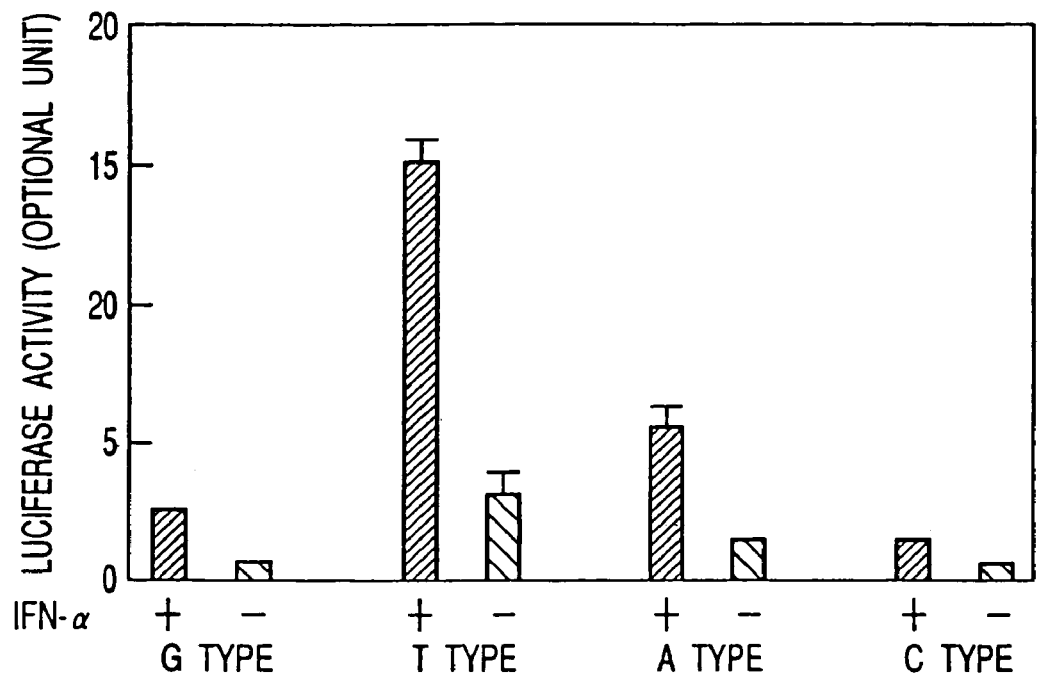
FIG. 7 is a graph showing comparison of responsibility to interferon β among MxA promoters having four kinds of SNP (T type, G type, A type and C type). The results were obtained in Hela cells using luciferase activity under the control of said promoters.
Figure 8:
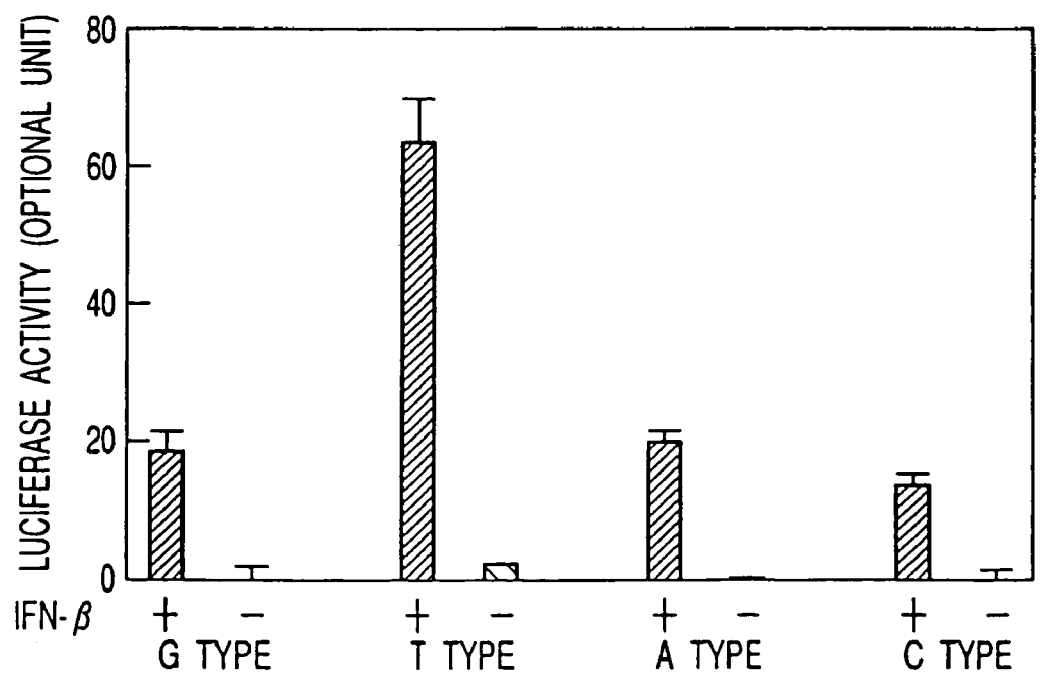
FIG. 8 is a graph showing comparison of responsibility to interferon β among MxA promoters having four kinds of SNP (T type, G type, A type and C type). The results were obtained in ovarian cancer cells using luciferase activity under the control of said promoters.

The results are shown in FIGS. 5 to 8. FIG. 5 is the example of induction in Hela cells using interferon α, FIG. 6 is the example of induction in ovary cancer cells using interferon α, FIG. 7 is the example of induction in Hela cells using interferon β, and FIG. 8 is the example of induction in ovary cancer cells using interferon β. In these figures, + indicates luciferase activity when interferon was added, and − indicates luciferase activity when interferon was not added. All the results are mean values of three experiments, and standard deviations are displayed using bars.

It is apparent from the figures that T type MxA promoter shows the highest values in all the cases. On the other hand, the response of HCV hepatitis patients having SNP of A and C types to interferon α and interferon β is low as in the case of G type, and thus, effect of the interferon therapy is predicted to be low.

EXAMPLE 3

Figure 9:
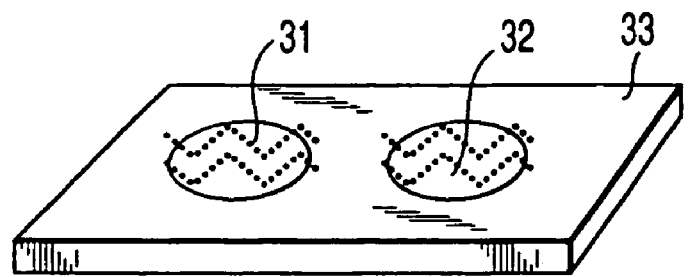
FIG. 9 shows a carrier for gene detection according to an embodiment of the present invention.

In the present example, the procedure for predicting validity of interferon therapy using the carrier for gene detection of the present invention is explained in reference to FIG. 9.

First, in order to prepare the carrier for gene detection, primers of Sequence ID Nos. 21 and 22 were used to amplify the T type fragment 31 which is a fragment of polynucleotide of Sequence ID No. 1 containing thymine at the SNP site, and the G type fragment 32 which is a polynucleotide of Sequence ID No. 2 containing guanine at the SNP site. The product is adjusted to give 2 μg/μL solutions using distilled water.

Next, equal amounts of 4 mg/mL nitrocellulose (DMSO solution) were added to the solution, and then, thermal denaturing were performed, followed by spotting the resultant solution on polylisine-coated slide glasses 33. After thorough drying, the spots were fixed by UV radiation to obtain carriers for gene detection on which T type fragment 31 and G type fragment 32 were immobilized.

Then, after amplification of the sample polynucleotide extracted from the blood of subject using primers of Sequence ID Nos. 20 and 21, the ECL labeling system of Pharmacia was used to carry out FITC labeling, and the sample was reacted with the previously prepared carriers for gene detection for 12 hours at 65° C. After reaction, signals were measured using a fluorescent detector.

As the result, fluorescent signal was observed from the spot in which T type fragment was immobilized, showing that the SNP of the sample polynucleotide used in the experiment was of T type.

EXAMPLE 4

Figure 10:
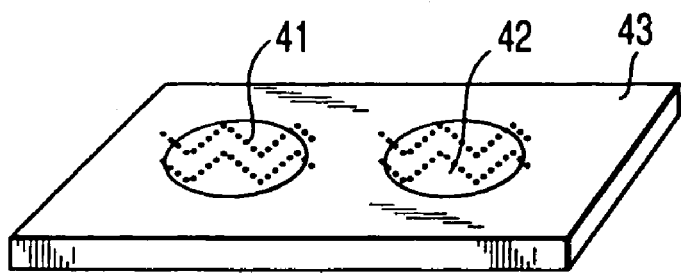
FIG. 10 shows a carrier for gene detection according to another embodiment of the present invention.

In the present example, examination using the carrier for gene detection on which the sample nucleotide fragment derived from a subject is immobilized is explained in reference to FIG. 10.

Fragments of polynucleotides derived from a subject, were amplified using primers of Sequence ID Nos. 21 and 22 (sample A: 41, sample B: 42), and the resultant product was adjusted to give 2 μg/μL solutions using distilled water. Then equal amounts of 4 mg/mL nitrocellulose (DMSO solution) were added to the solution. Following thermal denaturing treatment, the solution was spotted on polylisine-coated slide glasses 43. Further, after thorough drying, the spots were fixed by UV radiation to prepare the carrier for gene detection (a DNA chip).

Previously fluorescence labeled T type fragment that is a polynucleotide of Sequence ID No. 1 containing thymine at the SNP site (JOE label); previously fluorescence labeled G type fragment that is a polynucleotide of Sequence ID No. 2 containing guanine at the SNP site (5-FAM label); previously fluorescence labeled A type fragment that is a polynucleotide of Sequence ID No. 3 containing adenine at the SNP site (TAMRA label); and previously fluorescence labeled C type fragment that is a polynucleotide of Sequence ID No. 4 containing cytosine at the SNP site (ROX label) were reacted with the previously prepared DNA chip for 1 hour at 50° C.

After reaction, the signal was measured using a fluorescent detector. As the result, only the signal due to fluorescence of HEX was obtained, and the SNP of the sample polynucleotide was found to be of T type alone.

EXAMPLE 5

Figure 11:
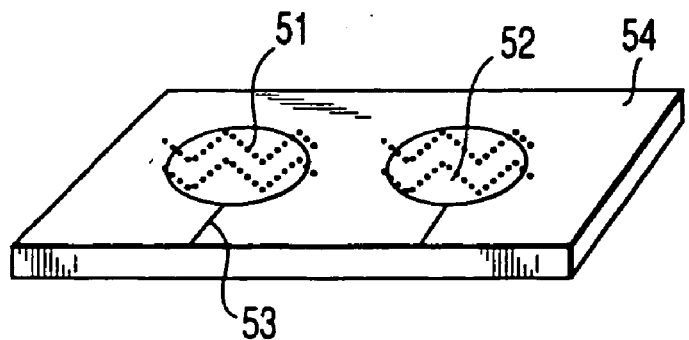
FIG. 11 shows a carrier for gene detection according to still another embodiment of the present invention.

In the present example, the carrier for gene detection using electrochemical detection is explained in reference to FIG. 11.

Primers of Sequence ID Nos. 21 and 22 were used to amplify T type fragment 51 of Sequence ID No. 1 and G type fragment 52 of Sequence ID No. 2, and the resultant product is adjusted to give 2 μg/μL solutions using distilled water. Then, thiol groups were introduced at the ends of the amplified products, by reaction with 2-hydroxyethyl disulfide and 1-cyclohexyl-3-(2-morpholinoethyl)-carbodiimide. They were spotted on a previously prepared gold electrode 53 and reacted for 1 hour while preventing drying.

The sample was amplified using primers of Sequence ID Nos. 21 and 22, thermally denatured, and then, reacted with a previously prepared DNA chip. After the reaction, voltammetry was carried out in a 10 μmol/L Hoechst 33258 solution to determine the oxidation current of the Hoechst 33258. As the result, a significant signal was obtained only from the electrode on which G type fragment was immobilized, indicating that the sample was G type.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of predicting whether interferon therapy will be effective for a hepatitis C virus infected individual, comprising:

obtaining a sample polynucleotide from the hepatitis C virus infected individual, wherein the sample polynucleotide comprises an interferon-stimulated response element, determining the nucleotide identity at a polymorphic position in the sample polynucleotide, wherein the polymorphic position is located at a position corresponding to that of the 455$^{th}$ nucleotide in SEQ ID NOs: 1-4, and predicting that interferon therapy for the individual is effective when the nucleotide identity of the single nucleotide polymorphism is thymine.

2. The method of claim 1, wherein the nucleotide identity at the polymorphic position is determined by restriction fragment length polymorphism.

3. The method of claim 1, further comprising amplifying the sample polynucleotide by polymerase chain reaction before determining the nucleotide identity at the polymorphic position in the sample polynucleotide.

4. A method for predicting whether interferon therapy will be ineffective for a hepatitis C virus infected individual, comprising:

obtaining sample polynucleotides from the hepatitis C virus infected individual, wherein the sample polynucleotides comprise a maternal and a paternal copy of an interferon-stimulated response element, determining the nucleotide identity of both copies of a polymorphic position in the sample polynucleotides, wherein the polymorphic position is located in the sample polynucleotides at a position corresponding to that of the 455$^{th}$ nucleotide in SEQ ID NOs: 1-4, and predicting that interferon therapy for the individual is not effective when the nucleotide identity of the single nucleotide polymorphism is guanine, adenine or cytosine on both genomic copies.

5. The method of claim 4, wherein the nucleotide identities of both copies of a polymorphic position in the sample polynucleotides, are determined by restriction fragment length polymorphism.

6. The method of claim 4, further comprising amplifying the sample polynucleotides, by polymerase chain reaction, before determining the nucleotide identity of both copies of a polymorphic position in the sample polynucleotides, in the sample polynucleotide.

7. The method of claim 4, which predicts whether α-interferon therapy will be ineffective.

8. The method of claim 4, which predicts whether β-interferon therapy will be ineffective.

9. The method of claim 1, which predicts whether α-interferon therapy will be effective.

10. The method of claim 1, which predicts whether β-interferon therapy will be effective.

11. A method for predicting whether interferon therapy will be effective for a hepatitis C virus infected individual, comprising:

obtaining sample polynucleotides from the hepatitis C virus infected individual, wherein the sample polynucleotides comprise a maternal and a paternal copy of an interferon-stimulated response element, determining the nucleotide identity of both copies of a polymorphic position in the sample polynucleotides, wherein the polymorphic position is located in the sample polynucleotides at a position corresponding to that of the 455$^{th}$ nucleotide in SEQ ID NOs: 1-4, and predicting that interferon therapy for the individual is effective when the nucleotide identity of the single nucleotide polymorphism is thymidine on one or both genomic copies.

12. The method of claim 11, comprising predicting that interferon therapy for the individual is effective when the nucleotide identity of the single nucleotide polymorphism is thymidine on one genomic copy.

13. The method of claim 11, comprising predicting that interferon therapy for the individual is effective when the nucleotide identity of the single nucleotide polymorphism is thymidine on both genomic copies.

* * * * *

SEQUENCE LISTING

<160> NUMBER OF SEQ ID NOS: 22

<210> SEQ ID NO 1
<211> LENGTH: 581
<212> TYPE: DNA
<213> ORGANISM: Homo sapiens

<400> SEQUENCE: 1

```
atgagccaga ctccagggag gcctagaagt gggcaagggg aaacgggaaa ggaggaagat      60
ggtatgggtg tgcctggtta ggggtgggag tgctggacgg agttcgggac aagaggggct     120
ctgcagccat tggcacacaa tgcctgggag tccctgctgg tgctgggatc atcccagtga     180
gccctgggag ggaactgaag accccccaatt accaatgcat ctgttttcaa aaccgacggg     240
gggaaggaca tgcctaggtt caaggatacg tgcaggcttg gatgactccg ggccattagg     300
gagcctccgg agcaccttga tcctcagacg ggcctgatga acgagcatc tgattcagca      360
ggcctgggtt cgggcccgag aacctgcgtc tcccgcgagt tcccgcgagg caagtgctgm     420
aggtgcgggg ccaggagcta ggtttcgttt ctgctcccgg agccgccctc agcacagggt     480
ctgtgagttt catttcttcg ccggcgcggg gcggggctgg gcgcggggtg aaagaggcga     540
accgagagcg gaggccgcac tccagcactg cgcagggacc g                        581
```

<210> SEQ ID NO 2
<211> LENGTH: 581
<212> TYPE: DNA
<213> ORGANISM: Homo sapiens

<400> SEQUENCE: 2

```
atgagccaga ctccagggag gcctagaagt gggcaagggg aaacgggaaa ggaggaagat      60
ggtatgggtg tgcctggtta ggggtgggag tgctggacgg agttcgggac aagaggggct     120
ctgcagccat tggcacacaa tgcctgggag tccctgctgg tgctgggatc atcccagtga     180
gccctgggag ggaactgaag accccccaatt accaatgcat ctgttttcaa aaccgacggg     240
gggaaggaca tgcctaggtt caaggatacg tgcaggcttg gatgactccg ggccattagg     300
gagcctccgg agcaccttga tcctcagacg ggcctgatga acgagcatc tgattcagca      360
ggcctgggtt cgggcccgag aacctgcgtc tcccgcgagt tcccgcgagg caagtgctgm     420
aggtgcgggg ccaggagcta ggtttcgttt ctgcgcccgg agccgccctc agcacagggt     480
ctgtgagttt catttcttcg ccggcgcggg gcggggctgg gcgcggggtg aaagaggcga     540
accgagagcg gaggccgcac tccagcactg cgcagggacc g                        581
```

<210> SEQ ID NO 3
<211> LENGTH: 581
<212> TYPE: DNA
<213> ORGANISM: Homo sapiens

<400> SEQUENCE: 3

```
atgagccaga ctccagggag gcctagaagt gggcaagggg aaacgggaaa ggaggaagat      60
ggtatgggtg tgcctggtta ggggtgggag tgctggacgg agttcgggac aagaggggct     120
ctgcagccat tggcacacaa tgcctgggag tccctgctgg tgctgggatc atcccagtga     180
gccctgggag ggaactgaag accccccaatt accaatgcat ctgttttcaa aaccgacggg     240
gggaaggaca tgcctaggtt caaggatacg tgcaggcttg gatgactccg ggccattagg     300
gagcctccgg agcaccttga tcctcagacg ggcctgatga acgagcatc tgattcagca      360
```

```
ggcctgggtt cgggcccgag aacctgcgtc tcccgcgagt tcccgcgagg caagtgctgm      420
aggtgcgggg ccaggagcta ggtttcgttt ctgcacccgg agccgccctc agcacagggt      480
ctgtgagttt catttcttcg ccggcgcggg gcggggctgg gcgcggggtg aaagaggcga      540
accgagagcg gaggccgcac tccagcactg cgcagggacc g                         581

<210> SEQ ID NO 4
<211> LENGTH: 581
<212> TYPE: DNA
<213> ORGANISM: Homo sapiens

<400> SEQUENCE: 4
atgagccaga ctccagggag gcctagaagt gggcaagggg aaacgggaaa ggaggaagat       60
ggtatgggtg tgcctggtta ggggtgggag tgctggacgg agttcgggac aagagggggct     120 ctgcagccat tggcacacaa tgcctgggag tccctgctgg tgctgggatc atcccagtga     180
gccctgggag ggaactgaag acccccaatt accaatgcat ctgttttcaa aaccgacggg     240
gggaaggaca tgcctaggtt caaggatacg tgcaggcttg gatgactccg ggccattagg     300
gagcctccgg agcaccttga tcctcagacg ggcctgatga acgagcatc tgattcagca      360 ggcctgggtt cgggcccgag aacctgcgtc tcccgcgagt tcccgcgagg caagtgctgm      420
aggtgcgggg ccaggagcta ggtttcgttt ctgccccccgg agccgccctc agcacagggt    480
ctgtgagttt catttcttcg ccggcgcggg gcggggctgg gcgcggggtg aaagaggcga     540
accgagagcg gaggccgcac tccagcactg cgcagggacc g                         581

<210> SEQ ID NO 5
<211> LENGTH: 16
<212> TYPE: DNA
<213> ORGANISM: Homo sapiens

<400> SEQUENCE: 5
ggtttcgttt ctgctc                                                       16

<210> SEQ ID NO 6
<211> LENGTH: 16
<212> TYPE: DNA
<213> ORGANISM: Homo sapiens

<400> SEQUENCE: 6
ggtttcgttt ctgcgc                                                       16

<210> SEQ ID NO 7
<211> LENGTH: 16
<212> TYPE: DNA
<213> ORGANISM: Homo sapiens

<400> SEQUENCE: 7
ggtttcgttt ctgcac                                                       16

<210> SEQ ID NO 8
<211> LENGTH: 16
<212> TYPE: DNA
<213> ORGANISM: Homo sapiens

<400> SEQUENCE: 8
ggtttcgttt ctgccc                                                       16

<210> SEQ ID NO 9
```

-continued

```
<211> LENGTH: 11
<212> TYPE: DNA
<213> ORGANISM: Homo sapiens

<400> SEQUENCE: 9
ttctgctccc g                                                                 11

<210> SEQ ID NO 10
<211> LENGTH: 11
<212> TYPE: DNA
<213> ORGANISM: Homo sapiens

<400> SEQUENCE: 10
ttctgcgccc g                                                                 11

<210> SEQ ID NO 11
<211> LENGTH: 11
<212> TYPE: DNA
<213> ORGANISM: Homo sapiens

<400> SEQUENCE: 11
ttctgcaccc g                                                                 11

<210> SEQ ID NO 12
<211> LENGTH: 11
<212> TYPE: DNA
<213> ORGANISM: Homo sapiens

<400> SEQUENCE: 12
ttctgccccc g                                                                 11

<210> SEQ ID NO 13
<211> LENGTH: 16
<212> TYPE: DNA
<213> ORGANISM: Homo sapiens

<400> SEQUENCE: 13
gagcagaaac gaaacc                                                            16

<210> SEQ ID NO 14
<211> LENGTH: 16
<212> TYPE: DNA
<213> ORGANISM: Homo sapiens

<400> SEQUENCE: 14
gcgcagaaac gaaacc                                                            16

<210> SEQ ID NO 15
<211> LENGTH: 16
<212> TYPE: DNA
<213> ORGANISM: Homo sapiens

<400> SEQUENCE: 15
gtgcagaaac gaaacc                                                            16

<210> SEQ ID NO 16
<211> LENGTH: 16
<212> TYPE: DNA
<213> ORGANISM: Homo sapiens

<400> SEQUENCE: 16
gggcagaaac gaaacc                                                            16
```

```
<210> SEQ ID NO 17
<211> LENGTH: 11
<212> TYPE: DNA
<213> ORGANISM: Homo sapiens

<400> SEQUENCE: 17
cgggagcaga a                                                                11

<210> SEQ ID NO 18
<211> LENGTH: 11
<212> TYPE: DNA
<213> ORGANISM: Homo sapiens

<400> SEQUENCE: 18
cgggcgcaga a                                                                11

<210> SEQ ID NO 19
<211> LENGTH: 11
<212> TYPE: DNA
<213> ORGANISM: Homo sapiens

<400> SEQUENCE: 19
cgggtgcaga a                                                                11

<210> SEQ ID NO 20
<211> LENGTH: 11
<212> TYPE: DNA
<213> ORGANISM: Homo sapiens

<400> SEQUENCE: 20
cgggggcaga a                                                                11

<210> SEQ ID NO 21
<211> LENGTH: 30
<212> TYPE: DNA
<213> ORGANISM: Artificial Sequence
<220> FEATURE:
<223> OTHER INFORMATION: Synthetic DNA

<400> SEQUENCE: 21
acacacccgt ttccaccctg gagaggccag                                             30

<210> SEQ ID NO 22
<211> LENGTH: 30
<212> TYPE: DNA
<213> ORGANISM: Artificial Sequence
<220> FEATURE:
<223> OTHER INFORMATION: Synthetic DNA

<400> SEQUENCE: 22
tgcgcagtgc tggagtgcgg cctccgctct                                             30
```